United States Patent
Feller, III et al.

(10) Patent No.: US 8,357,180 B2
(45) Date of Patent: *Jan. 22, 2013

(54) THIN FILM METALLIC DEVICE FOR PLUGGING ANEURYSMS OR VESSELS

(75) Inventors: Frederick R. Feller, III, Maple Grove, MN (US); Juan A. Lorenzo, Davie, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 999 days.

This patent is subject to a terminal disclaimer.

(21) Appl. No.: 11/662,849

(22) PCT Filed: Sep. 16, 2005

(86) PCT No.: PCT/US2005/033404
§ 371 (c)(1),
(2), (4) Date: Mar. 14, 2007

(87) PCT Pub. No.: WO2006/034153
PCT Pub. Date: Mar. 30, 2006

(65) Prior Publication Data
US 2008/0097495 A1      Apr. 24, 2008

Related U.S. Application Data

(60) Provisional application No. 60/610,784, filed on Sep. 17, 2004.

(51) Int. Cl.
*A61M 29/00*     (2006.01)
(52) U.S. Cl. .......................... 606/213; 606/194; 606/157
(58) Field of Classification Search .................. 606/157, 606/158, 151, 213, 194, 200, 191, 195, 198; 623/23.72, 11.11, 1.39, 1.15, 1.3; 128/830, 128/831, 843; 600/32
See application file for complete search history.

(56) References Cited

U.S. PATENT DOCUMENTS

| | | | | |
|---|---|---|---|---|
| 5,064,435 A | * | 11/1991 | Porter | 623/23.7 |
| 5,108,420 A | * | 4/1992 | Marks | 606/213 |
| 5,139,480 A | * | 8/1992 | Hickle et al. | 604/8 |
| 5,334,216 A | | 8/1994 | Vidal et al. | |
| 5,540,713 A | | 7/1996 | Schnepp-Pesch et al. | |
| 5,656,036 A | | 8/1997 | Palmaz | |
| 5,755,772 A | * | 5/1998 | Evans et al. | 128/898 |
| 5,861,003 A | * | 1/1999 | Latson et al. | 606/213 |
| 5,908,409 A | | 6/1999 | Rinehart et al. | |
| 5,928,260 A | * | 7/1999 | Chin et al. | 606/200 |
| 6,120,534 A | * | 9/2000 | Ruiz | 623/1.19 |
| 6,146,396 A | * | 11/2000 | Konya et al. | 606/159 |
| 6,168,622 B1 | | 1/2001 | Mazzocchi | |
| 6,193,748 B1 | | 2/2001 | Thompson et al. | |
| 6,221,086 B1 | | 4/2001 | Forber | |
| 6,375,668 B1 | * | 4/2002 | Gifford et al. | 606/200 |
| 6,428,558 B1 | * | 8/2002 | Jones et al. | 606/200 |
| 6,432,116 B1 | | 8/2002 | Callister et al. | |

(Continued)

*Primary Examiner* — Julian Woo
*Assistant Examiner* — Christopher L Templeton

(57) ABSTRACT

Thin film metallic devices implantable within a human subject for occlusion of an aneurysm or blood vessel are provided. The devices are movable from a porous, elongated, collapsed configuration for delivery to a deployed configuration within the body. The pores telescope as the device moves to its deployed configuration, which causes the device to longitudinally foreshorten and radially expand, while also decreasing in porosity for preventing blood flow. The occlusion devices may be either self-supporting or supported by a strut structure. Additionally, the occlusion devices may comprise a plurality of layers having unaligned pore systems which further reduce porosity in the deployed configuration.

23 Claims, 2 Drawing Sheets

U.S. PATENT DOCUMENTS

| | | | |
|---|---|---|---|
| 6,463,317 | B1 | 10/2002 | Kucharczyk et al. |
| 6,599,308 | B2 | 7/2003 | Amplatz |
| 6,669,721 | B1 | 12/2003 | Bose et al. |
| 6,746,890 | B2 | 6/2004 | Gupta et al. |
| 6,821,291 | B2 * | 11/2004 | Bolea et al. ............... 623/1.11 |
| 6,938,668 | B2 | 9/2005 | Whicher |
| 7,300,457 | B2 * | 11/2007 | Palmaz ..................... 623/1.13 |
| 7,811,300 | B2 * | 10/2010 | Feller et al. ................. 606/157 |
| 7,875,044 | B2 * | 1/2011 | Feller et al. ................. 606/157 |
| 2001/0039449 | A1 | 11/2001 | Johnson et al. |
| 2002/0151958 | A1 | 10/2002 | Chuter |
| 2003/0066533 | A1 | 4/2003 | Loy |
| 2003/0125798 | A1 * | 7/2003 | Martin ....................... 623/1.13 |
| 2003/0171739 | A1 | 9/2003 | Murphy et al. |
| 2003/0171774 | A1 * | 9/2003 | Freudenthal et al. ......... 606/213 |
| 2003/0216804 | A1 * | 11/2003 | DeBeer et al. ............... 623/1.15 |
| 2004/0098094 | A1 * | 5/2004 | Boyle et al. ................. 623/1.13 |
| 2004/0143288 | A1 | 7/2004 | Searle |
| 2005/0033418 | A1 * | 2/2005 | Banas et al. ................. 623/1.49 |
| 2005/0182481 | A1 * | 8/2005 | Schlick et al. ............... 623/1.15 |
| 2006/0069428 | A1 * | 3/2006 | Feller, III ................... 623/1.44 |
| 2007/0270902 | A1 * | 11/2007 | Slazas et al. ................. 606/200 |

* cited by examiner

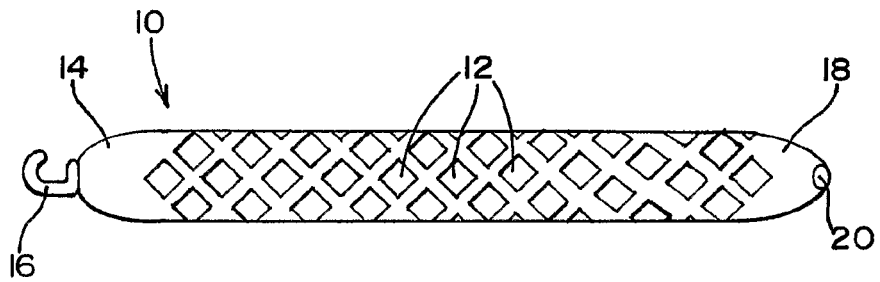
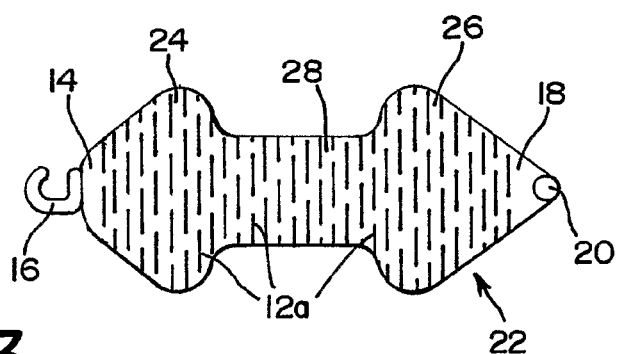
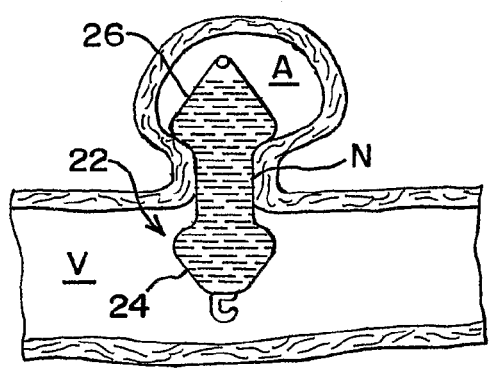
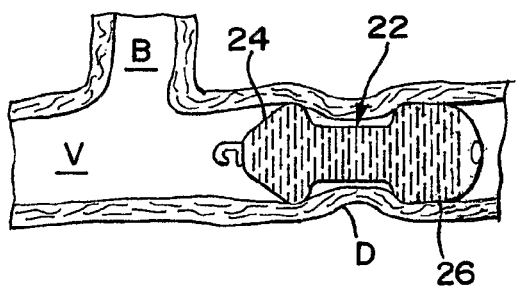
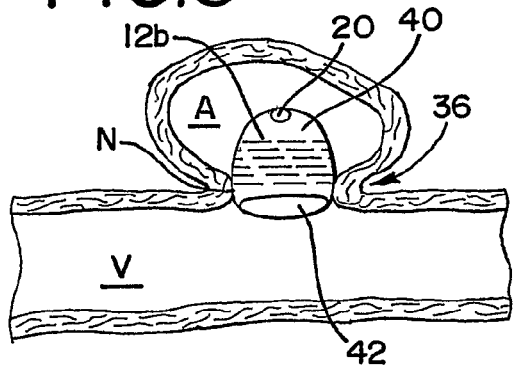
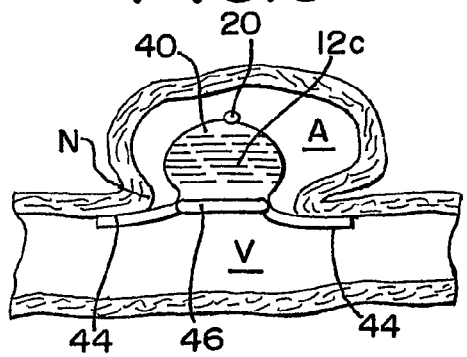

THIN FILM METALLIC DEVICE FOR PLUGGING ANEURYSMS OR VESSELS

CROSS REFERENCE TO RELATED APPLICATION

This application claims priority from provisional patent application Ser. No. 60/610,784, filed Sep. 17, 2004, which is hereby incorporated herein by reference.

FIELD OF THE INVENTION

This invention generally relates to medical devices that are implantable within a human subject and that have occlusion capabilities that are especially suitable for use as medical device plugs for aneurysms or for defective or diseased body vessels. These types of devices have porosity which, upon deployment, is automatically reduced or eliminated in order to exhibit an enhanced occlusion capability.

DESCRIPTION OF RELATED ART

Medical devices that can benefit from the present invention include those that are characterized by hollow interiors and that are introduced endoluminally and expand when deployed so as to plug up a location of concern within the patient. These are devices that move between collapsed and expanded conditions or configurations for ease of deployment through catheters and introducers. The present disclosure focuses upon occlusion devices for aneurysms or other defects or diseased locations within the vasculature, explicitly including those that are sized, shaped and constructed for neurovascular use.

An aneurysm is an abnormal bulge or ballooning of the wall of a blood vessel. Typically, an aneurysm develops in a weakened wall of an arterial blood vessel. The force of the blood pressure against the weakened wall causes the wall to abnormally bulge or balloon outwardly. One detrimental effect of an aneurysm is that the aneurysm may apply undesired pressure to tissue surrounding the blood vessel. This pressure can be extremely problematic, especially in the case of a cranial aneurysm where the aneurysm can apply pressure against sensitive brain tissue. Additionally, there is also the possibility that the aneurysm may rupture or burst, leading to more serious medical complications including mortality.

When a patient is diagnosed with an unruptured aneurysm, the aneurysm is treated in an attempt to reduce or lessen the bulging and to prevent the aneurysm from rupturing. Unruptured aneurysms have traditionally been treated by what is commonly known in the art as "clipping." Clipping requires an invasive surgical procedure wherein the surgeon makes incisions into the patient's body to access the blood vessel containing an aneurysm. Once the surgeon has accessed the aneurysm, he or she places a clip around the neck of the aneurysm to block the flow of blood into the aneurysm which prevents the aneurysm from rupturing. While clipping may be an acceptable treatment for some aneurysms, there is a considerable amount of risk involved with employing the clipping procedure to treat cranial aneurysms because such procedures require open brain surgery.

More recently, intravascular catheter techniques have been used to treat cranial aneurysms because such techniques do not require cranial or skull incisions, i.e., these techniques do not require open brain surgery. Typically, these techniques involve using a catheter to deliver embolic devices to a preselected location within the vasculature of a patient. For example, in the case of a cranial aneurysm, methods and procedures, which are well known in the art, are used for inserting and guiding the distal end of a delivery catheter into the vasculature of a patient to the site of the cranial aneurysm. A coil-like vascular occlusion device then is attached to the end of a pusher member which pushes the occlusion device through the catheter and out of the distal end of the catheter where the occlusion device is delivered into the aneurysm.

Once the occlusion device has been deployed within the aneurysm, the blood clots on the occlusion device and forms a thrombus. The thrombus forms an occlusion which seals off the aneurysm, preventing further ballooning or rupture. In some instances, the deployment procedure is repeated until multiple coil-like occlusion devices are deployed within the aneurysm. With these aneurysm-packing approaches, typically, it is desired to deploy enough coil-like devices to obtain a packing density of about 20% or more, preferably about 35% and more if possible.

The most common coil-like vascular occlusion devices are embolic coils. Embolic coils typically are constructed from a metal wire which has been wound into a helical shape. One of the drawbacks of embolic coils for some applications is that they do not provide a large surface area for blood to clot thereto. Additionally, the embolic coil may be situated in such a way that there are relatively considerable gaps between the coil and the aneurysm wall or adjacent coils in which blood may freely flow. The addition of extra coils into the aneurysm does not always solve this problem because deploying too many coils into the aneurysm may lead to an undesired rupture.

Therefore, there remains a need that is recognized and addressed according to the present invention for an occlusion device which can function alone in order to plug an entrance into an aneurysm or other vessel defect with the objective of enhancing the effectiveness of the occlusion device in stopping or severely restricting blood flow into the diseased space or aneurysm, without increasing the risk of rupturing the aneurysm.

Examples of devices which follow a general approach of aneurysm plugging include Mazzocchi U.S. Pat. No. 6,168,622, hereby incorporated by reference hereinto. Metal fabric strands are given a bulbous shape which is intended to occupy substantial space within the aneurysm, while an "anchor" is intended to hold the device in place. Strands of metals including nickel-titanium alloys generally known as "nitinol" metal alloys are proposed for making into metal fabric by braiding techniques. The occlusion capabilities of the braided metal are determined during the manufacturing process.

Technologies other than braiding have been used in the medical device field. These include using thin film technologies. Current methods of fabricating thin films (on the order of several microns thick) employ material deposition techniques. These methods are known to make films into basic shapes, such as by depositing onto a mandrel or core so as to make thin films having the shape of the mandrel or core, such as geometric core shapes until the desired amount has built up. Traditionally, a thin film is generated in a simple (oftentimes cylindrical, conical, or hemispherical) form and heat-shaped to create the desired geometry. One example of a known thin film vapor deposition process can be found in Banas and Palmaz U.S. Patent Application Publication No. 2005/0033418, which is hereby incorporated herein by reference.

Methods for manufacturing three-dimensional medical devices using planar films have been suggested, as in U.S. Pat. No. 6,746,890 (Gupta et al.), which is hereby incorporated herein by reference. The method described in Gupta et al. requires multiple layers of film material interspersed with sacrificial material. Accordingly, the methods described therein are time-consuming and complicated because of the need to alternate between film and sacrificial layers.

For some implantable medical devices, it is preferable to use a porous structure. Typically, the pores are added by masking or etching techniques or laser or water jet cutting. When occlusion devices are porous, especially for intercranial use, the pores are extremely small and these types of methods are not always satisfactory and can generate accuracy issues. Approaches such as those proposed by U.S. Patent Application Publication No. 2003/0018381 of Whitcher et al., which is hereby incorporated herein by reference, include vacuum deposition of metals onto a deposition substrate which can include complex geometrical configurations. Microperforations are mentioned for providing geometric distendability and endothelization. Such microperforations are said to be made by masking and etching.

An example of porosity in implantable grafts is Boyle, Marton and Banas U.S. Patent Application Publication No. 2004/0098094, which is hereby incorporated by reference hereinto. This publication proposes endoluminal grafts having a pattern of openings, and indicates different orientations thereof could be practiced. Underlying stents support a microporous metallic thin film. Also, Schnepp-Pesch and Lindenberg U.S. Pat. No. 5,540,713, which is hereby incorporated by reference hereinto, describes an apparatus for widening a stenosis in a body cavity by using a stent-type of device having slots which open into diamonds when the device is radially expanded.

A problem to be addressed is to provide a plug-like occlusion device that can be delivered endoluminally in intercranial applications with a relatively high porosity while implanting and locating same at the proper site generally at the mouth of an occlusion, yet after deployment minimizes or eliminates the porosity so as to provide an immediate occlusive function to "plug" the aneurysm or vessel defect and control or stop blood flow into the diseased site.

Accordingly, a general aspect or object of the present invention is to provide an occlusion device having porosity properties and that performs a plugging function and substantially reduces its porosity on deployment at the diseased site.

Another aspect or object of this invention is to provide a method for plugging an aneurysm or other vessel defect that can be performed in a single endoluminal procedure and that positions an occlusion device for effective blood flow blockage into the diseased location.

Another aspect or object of this invention is to provide an improved occlusion device that incorporates thin film metal deposition technology in preparing neurovascular occlusion devices which exhibit porosity during deployment that is greatly reduced to a low porosity condition when properly positioned for occlusion.

Another aspect or object of the present invention is to provide an occlusion device having a three-dimensional configuration that has shape features set thereinto that form upon deployment and that are designed for plugging openings of diseased vasculature.

Other aspects, objects and advantages of the present invention, including the various features used in various combinations, will be understood from the following description according to preferred embodiments of the present invention, taken in conjunction with the drawings in which certain specific features are shown.

SUMMARY OF THE INVENTION

In accordance with the present invention, an occlusion device is provided that has a thin film structure that has a contracted or collapsed configuration which facilitates endoluminal deployment as well as an expanded or deployed configuration. When in at least the deployed configuration, the thin film is shaped with a converging end of reduced cross-sectional extent when compared with the rest of the deployed device. Such deployed shapes can be generally closed end types and include a "dog bone" type, a flange type and a plug type.

Porosity is provided in the radially contracted configuration in the form of slots that are generally open when the device is stretched longitudinally. These slots close substantially or fully upon deployment when the thin film foreshortens and expands radially to shrink the slots to a smaller profile. This slot closure upon expansion provides a low enough porosity to occlude blood flow to an aneurysm or vessel being treated.

In making the thin film, a core or mandrel is provided which is suited for creating a thin film by a physical vapor deposition technique, such as sputtering. A film material is deposited onto the core to form a seemless or continuous three-dimensional layer. The thickness of the film will depend on the particular film material selected, conditions of deposition and so forth. Typically, the core then is removed by chemically dissolving the core, or by other known methods. Manufacturing variations allow the forming of multiple layers of thin film material or a thicker layer of deposited material if desired.

Special application for the present invention has been found for creating porous occlusion devices which have a thin film structure and automatic porosity reduction upon deployment as plug-type devices, and methods also are noted. However, it will be seen that the products and methods described herein are not limited to particular medical devices or methods of manufacture or particular surgical applications.

BRIEF DESCRIPTION OF THE DRAWINGS

FIG. 1 is a front elevational view of an occlusion device according to the present invention, in a collapsed configuration;

FIG. 2 is a front elevational view of a "dog bone"-shaped occlusion device in a deployed configuration;

FIG. 3 is a front elevational view of the occlusion device of FIG. 2 deployed in an aneurysm;

FIG. 4 is a front elevational view of the occlusion device of FIG. 2 deployed in a blood vessel;

FIG. 5 is a front elevational view of a plug-type occlusion device deployed in an aneurysm;

FIG. 6 is a front elevational view of a flange-type occlusion device deployed in an aneurysm;

DESCRIPTION OF THE PREFERRED EMBODIMENTS

Figure 7:
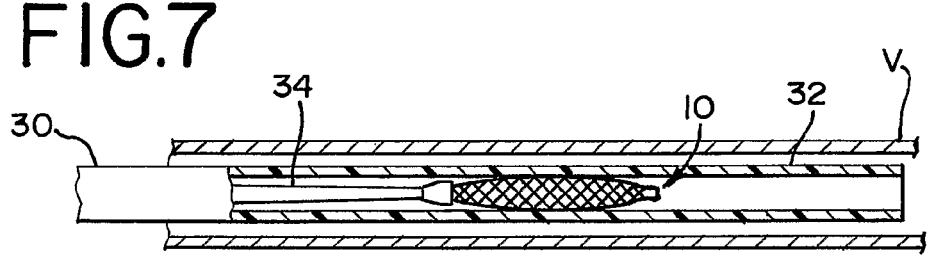
FIG. 7 is a cross-sectional view of an occlusion device in a collapsed configuration within a catheter or introducer.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 1 illustrates an occlusion device 10 in a collapsed position. The occlusion device 10 preferably comprises a thin film formed by physical vapor deposition onto a core or mandrel, as is well-known to those skilled in the art. Most preferably, a thin film of nitinol (which encompasses alloys of nickel and titanium), or other material which preferably has the ability to take on a shape that had been imparted to it during manufacture, is formed. When nitinol material is used in forming the thin film, the thin film can be at the martensite state. In addition, the thin film when made of nitinol or materials having similar shape memory properties may be austenite with a transition from martensite to austenite, typically when the device is raised to approximately human body temperature, or in the range of about 95 F. to 100 F.

In making the thin film, this selected material is sputter-deposited onto a core, which core is then removed by chemical etching or the like. Examples of this type of deposition are found in US Published Patent Application No. 2003/0018381, No. 2004/0098094 and No. 2005/0033418, incorporated herein by reference. Nitinol is a preferred film material because of its superelastic and shape memory properties, but other known biocompatible compositions with similar characteristics may also be used.

The thickness of the thin film mesh depends on the film material selected, the intended use of the device, the support structure, and other factors. For example, a thin film of nitinol is preferably between about 0.1 and 250 microns thick and typically between about 1 and 30 microns thick. More preferably, the thickness of the thin film mesh is between about 1 and 10 microns or at least about 0.1 microns but less than about 5 microns. A mesh associated with a support structure may be thinner than a self-supporting thin film mesh.

The occlusion device 10 has a plurality of pores or openings 12 according to an aspect of the present invention. The pores 12 may be formed by any known means, but are preferably formed using laser-cutting. The illustrated pores 12 are shown in FIG. 1 with generally identical diamond-shaped openings which are arranged in a uniform pattern along the length of the occlusion device 10, but they may assume other open profiles and be arranged randomly or in selected non-uniform patterns, depending on the intended use. The occlusion device 10 also includes a generally closed proximal end 14, which preferably includes an engagement member or hook 16, and a generally closed distal end 18 that is atraumatically sealed shut by a plasma weld 20 or other suitable seal.

In use, the pores 12 allow the associated portion of the occlusion device 10 to expand radially. For example, FIG. 2 shows an occlusion device which assumes a "dog bone" shape 22 in a deployed configuration. When implanted in the body, the occlusion device moves from the elongated, collapsed configuration of FIG. 1 to the foreshortened, deployed configuration of FIG. 2, while the pores move from the open configuration 12 of FIG. 1 to the generally closed configuration 12a of FIG. 2. Compared to the open configuration 12, the pores in the generally closed configuration 12a resemble closed slits, which provide a decreased porosity and are intended to prevent the flow of blood and other bodily fluids through the occlusion device. Thrombus development occurs and occlusion results as generally appreciated in the art.

It will be appreciated that not all of the pores 12 need move to a generally closed configuration 12a in order to provide an occlusive effect. For example, the "dog bone" occlusion device 22 will typically provide a satisfactory occlusive effect in the applications of FIGS. 3 and 4 if either one of the bulbous portions 24 and 26 acts as a plug with pores in a generally closed configuration 12a.

The "dog bone" occlusion device 22 of FIGS. 2-4 has two bulbous portions 24 and 26, which are separated by a relatively narrow portion 28. The illustrated bulbous portions 24 and 26 are generally identical, but they may be sized or configured differently, depending on the intended application. This deployed configuration is typically achieved by heating a nitinol thin film mesh or other shape memory material when on a shaping mandrel until it reaches an austenite condition, whereby it is heat-set into the desired "dog bone" shape.

Typically, such memory "setting" is adequate to achieve the desired expanded shape of the device. It can be possible to assist this expanded shaping by varying slit or pore size. For example, the elasticity of the mesh can be supplemented in the bulbous portions 24 and 26 by overlaying those portions with relatively large slits that telescope to allow for enhanced radial expansion when the occlusion device 22 moves from a collapsed configuration to a deployed configuration. In contrast, less radial expansion is desired in the narrow portion 26, so smaller slits that telescope to a lesser extent may be used. Alternatively, if even less radial expansion is required, the narrow portion 26 may be devoid of slits, which means that the amount of expansion which results is due to the characteristics of the thin film material unaided by slits in the material.

Figure 8:
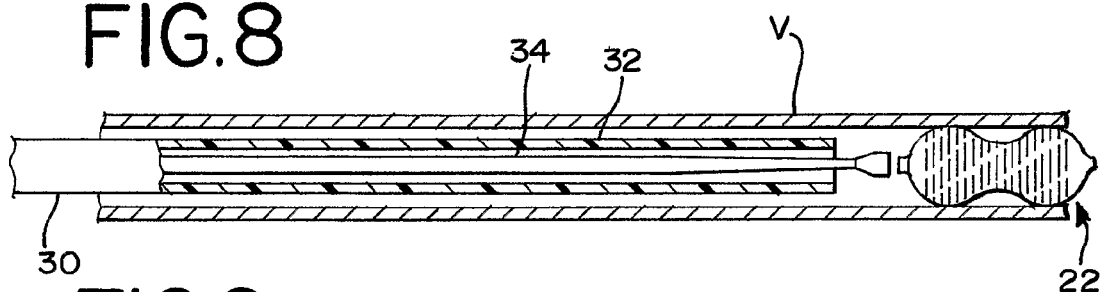
FIG. 8 is a cross-sectional view of the occlusion device of FIG. 7 in a deployed configuration within a blood vessel.

The occlusion device is configured and sized for transport within a catheter or introducer 30 in a collapsed configuration 10, as illustrated in FIGS. 7 and 8. In general, the occlusion device 10 is placed at a downstream end 32 of a catheter 30, which catheter 30 is introduced to the interior of a blood vessel V. The downstream end 32 is positioned adjacent to a region of the blood vessel V which is to be occluded, then a plunger or pusher member 34 ejects the occlusion device 10 into the target region. This may be achieved by moving the pusher member 34 distally, moving the catheter 30 in a retrograde direction, or a combination of both types of movement.

Preferably, the occlusion device 10 is comprised of a shape memory material, such as nitinol, which will move to a deployed configuration 22 upon exposure to living body temperatures, as shown in FIG. 8. When the occlusion device has been placed, the catheter 30 and plunger 34 are thereafter removed from the vessel V, and the occlusion device is left at its deployed location, as shown in FIG. 4.

FIGS. 7 and 8 illustrate deployment of a "dog bone"-shaped occlusion device 22 to a blood vessel V, but the described method can be applied to other body locations, such as within the aneurysm A of FIG. 3, and at a location in a vessel V that is in the vicinity of a branch B and a diseased area D, as shown in FIG. 4. Also, other occlusion device geometries can be used. For example, FIGS. 5 and 6 illustrate a plug-type occlusion device 36 and a flange-type occlusion device 38, respectively, applied to an aneurysm A.

The plug-type occlusion device 36 can be understood with reference to the "dog bone" occlusion device of FIG. 2. The plug-type occlusion device 36 is comparable to the bulbous portion 26, with some or all of the narrow portion 28 and other bulbous portion 24 being essentially omitted when compared to the shape of the device shown in FIG. 2. In the deployed configuration of FIG. 5, the plug-type occlusion device 36 has an upper end 40, which is closed by a plasma weld 20 or other atraumatic means, and an open lower end 42. Intermediate the distal and proximal end portions 40 and 42, respectively, are a plurality of slits or pores, which are shown in a generally closed configuration 12b in FIG. 5.

In use, the plug-type occlusion device 36 is delivered to the aneurysm A in an elongated, collapsed configuration, where it is released from a catheter or introducer and allowed to move to a foreshortened, deployed configuration, as in FIG. 3. In the illustrated deployed configuration, the slits or pores close, which causes the proximal end portion 42 to radially expand to engage a neck portion N of the aneurysm A. The deployed configuration with generally closed slits or pores 12b has a decreased porosity and prevents the flow of blood into the aneurysm A, which fosters thrombosis and reduces the risk that the aneurysm will rupture.

The flange-type occlusion device 38 of FIG. 6 is a variation of the plug-type occlusion 36 of FIG. 5. The principal difference therebetween is the addition of a skirt or flange 44 extending laterally outward from the proximal end portion 46. This end portion can be reduced in cross-sectional size to comply with the neck of aneurysm A, as shown in FIG. 6. Thus, in the illustrated deployed configuration of FIG. 6, the reduced open proximal end portion 46 fits within the aneurysm neck N, and need not fully engage it. The flange 44 remains within the vessel V and overlays the neck N, thereby acting in concert with the effectively non-porous body portion 48 as a patch that prevents blood flow into the aneurysm A. Preferably the flange 44 is sufficiently rigid that it will not buckle and cause the occlusion device 38 to migrate into the aneurysm A. When closed, the slits 12c minimize flow into the aneurysm A and result in its occlusion.

As described previously with regard to the "dog bone" shaped occlusion device 22, the slits or pores of the plug-type and flange-type occlusion devices 36 and 38 may be of different sizes and locations. Although in typical application this variation is not required, it may facilitate the desired expanded shaping, depending on the desired amount of radial expansion and longitudinal foreshortening required at any particular location of the device.

If the occlusion device includes a hook 16, as illustrated in FIGS. 1-4, the device can be removed from the body or readjusted within the vessel after deployment. The distal end 18 of the occlusion device is inserted into the target region prior to full removal of the proximal end 14 from the distal catheter end 32 in order to minimize the risk of damage to the vasculature and to facilitate removal or location adjustment if needed. To remove or adjust the location of the occlusion device, the process of FIGS. 7 and 8 is essentially reversed, by replacing the pusher member 34 with a pulling member, not illustrated, of known construction to engage the hook 16 or the like and to pull the occlusion device into the catheter 30 and have the catheter engage the walls of the device to reduce its radial size. When the occlusion device is back in the catheter 30, the catheter 30 then is removed from the vessel V or used to reposition the occlusion device.

Figure 9:
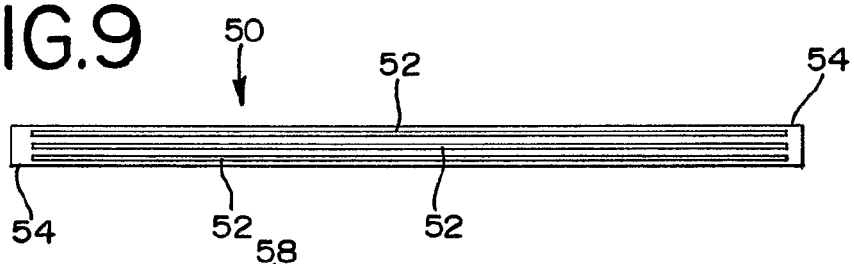
FIG. 9 is a front elevational view of a tube used to form the support struts of an alternate embodiment.
Figure 10:
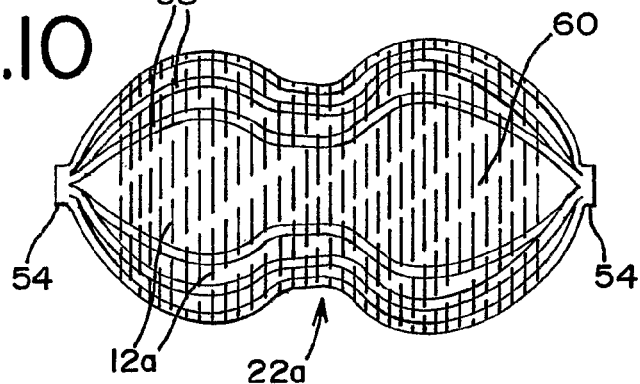
FIG. 10 is a front elevational view a "dog bone"-shaped occlusion device according to an alternate embodiment.

According to an alternate embodiment of the present invention, the described occlusion devices may be provided with a support structure, similar to that described in U.S. Pat. No. 6,428,558 (Jones and Mitelberg), which is hereby incorporated herein by reference. FIG. 9 shows a generally hollow tube 50 which may be used to make an internal support structure for a "dog bone"-shaped occlusion device 22a, as illustrated in FIG. 10. The tube 50 is preferably comprised of nitinol or another shape memory material having a wall between about 70 and 250 microns thick, most preferably between about 175 and 225 microns thick. The tube also has at least one region with a plurality of longitudinal cuts 52 and two uncut end portions 54.

In assembling the tube and the thin film, the tube 50 is placed within a mold and a compressive force is applied to the ends 54 until the cuts 52 buckle outward to define the struts 58 of FIG. 10. A similarly shaped mold is used to configure a thin film mesh 60 as illustrated in FIG. 10. Thereafter, when it is desired to provide an occlusion device having an internal support structure, the tube 50 is returned to its FIG. 9 configuration, and the molded thin film mesh 60 is placed thereover and sealed at least along the ends 54, typically while both the tube 50 and the thin film mesh 60 are in an expanded mode such as that of FIG. 10. Alternatively, the thin film mesh can be positioned inside the tube to provide a device having an external support structure. As a further option, the tube can be positioned between thin film mesh layers to provide an occlusion device having an encapsulated support structure.

The mesh 60 is preferably a biocompatible, flexible material and may be thinner than the thin film of FIGS. 1-6, because it is not required to support itself. The mesh 60 does include a slit or pore structure similar to the self-supporting embodiments, whereby the pores move to a generally closed slit configuration when the occlusion device 22a is deployed, as illustrated in FIG. 10. While this aspect of the present invention is shown and described with reference to a "dog bone"-shaped occlusion device, the shape and configuration of the cuts along the tube, as well as the shape of the molds, can be varied so that it can be applied to other occlusion devices according to the present invention. For example, if the slots or cuts 52 are interrupted by an uncut section, a waist will form at the uncut section. In other words, the absence of the cut or slotted aspect at a given area will minimize radial expansion thereat while the cut or slotted lengths will radially expand.

Figure 11:
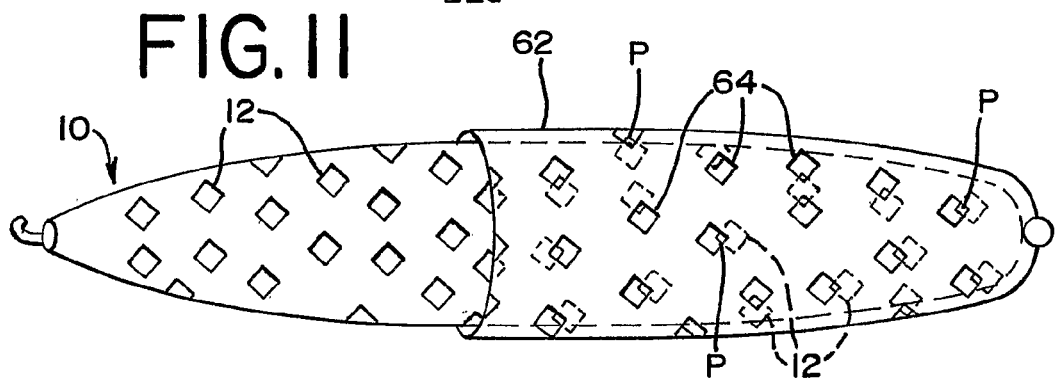
FIG. 11 is a front elevational view of an occlusion device in a collapsed configuration according to an alternate embodiment, with portions broken away for clarity.

According to another alternate embodiment of the present invention, the described occlusion devices may be created with an additional outer thin film layer 62, as illustrated in FIG. 11. An occlusion device 10 according to FIG. 1 is nested within a porous thin film layer 62, which is partially broken away in FIG. 11. These layers operate according to the principles described above. Preferably the two layers 10 and 62 have differing pore patterns or at least pore patterns that are out of phase with each other, such that the pores 12 of the inner layer 10 are misaligned with the pores 64 of the outer layer 62, thereby decreasing the effective pore size P of the layered occlusion device 66. As a result, the layered occlusion device 66 will have substantially the same radially expansive properties according to the present invention, while providing an even lower porosity in the deployed configuration, which improves the occlusive properties. This embodiment is useful when slitting technology does not provide pore sizing as small as may be desired in some circumstances.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A thin film occlusion device for occluding at least a portion of a body vessel in a human subject, comprising: a thin film including a distal end portion having a substantially closed end configuration; a proximal end portion; a body portion extending between said distal end portion and said proximal end portion; and a plurality of slot members associated with at least a selected one of said body portion, distal end portion, and proximal end portion, wherein said slot members are in a generally open condition when the occlusion device is in a collapsed orientation suitable for passage through a medical delivery apparatus, and wherein said slot members are in a generally closed condition with radial expansion movement of the occlusion device to a deployed orientation for occlusion action within a body vessel.

2. The thin film occlusion device of claim 1, further comprising an engagement member associated with said proximal end portion for selective removal of the occlusion device from a body vessel or repositioning of the occlusion device in a body vessel.

3. The thin film occlusion device of claim 1, further comprising a support structure of the occlusion device for supporting at least one of said distal end portion, proximal end portion, and body portion.

4. The thin film occlusion device of claim 1, further comprising a plurality of thin film layers, each having a plurality of slot members.

5. The thin film occlusion device of claim 1, wherein at least the selected one of said body portion, distal end portion, and proximal end portion longitudinally foreshorten and radially expand upon movement of the occlusion device to the deployed configuration.

6. The thin film occlusion device of claim 1, wherein said body portion, distal end portion, and proximal end portion are comprised of a material having shape memory properties.

7. The thin film occlusion device of claim 6, wherein said material having shape memory properties is nitinol.

8. The thin film occlusion device of claim 1, wherein said body portion, distal end portion, and proximal end portion are comprised of a material having a thickness greater than about 0.1 microns and less than about 5 microns.

9. A thin film occlusion device for occluding at least a portion of a body vessel in a human subject, comprising: a thin film including a distal end portion having a substantially closed end configuration; a proximal end portion; a body portion extending between said distal end portion and said proximal end portion; and a plurality of pores associated with at least a selected one of said distal end portion, proximal end portion, and body portion, wherein the occlusion device is movable between a collapsed orientation for delivery by a medical implantation apparatus and a radially expanded deployed orientation within a body vessel, and wherein the porosity of at least the selected one of said distal end portion, proximal end portion, and body portion is greater in said collapsed orientation than in said deployed orientation.

10. The thin film occlusion device of claim 9, further comprising a flange member associated with and outwardly extending with respect to said proximal end portion.

11. The thin film occlusion device of claim 9, further comprising a support structure within an interior of the occlusion device for supporting at least one of said distal end portion, proximal end portion, and body portion.

12. The thin film occlusion device of claim 9, further comprising a plurality of thin film layers, each having a plurality of pores, and at least some of said pores of one of said film layers are out of alignment with any pore of another of said film layers.

13. The thin film occlusion device of claim 9, wherein at least the selected one of said body portion, distal end portion, and proximal end portion longitudinally foreshorten and radially expand upon movement of the occlusion device to the deployed configuration.

14. The thin film occlusion device of claim 9, wherein said body portion, distal end portion, and proximal end portion are comprised of a material having shape memory properties.

15. The thin film occlusion device of claim 14, wherein said material having shape memory properties is nitinol.

16. A thin film occlusion device for occluding at least a portion of a body vessel in a human subject, comprising: a thin film including a distal end portion having a substantially closed end configuration; a proximal end portion having a substantially closed end configuration; a body portion extending between said distal end portion and said proximal end portion; and a plurality of pores associated with said distal end portion and said proximal end portion, wherein said pores are capable of movement from a generally open condition to a generally closed condition and wherein the movement causes at least said distal end portion and said proximal end portion to longitudinally foreshorten and radially expand.

17. The thin film occlusion device of claim 16, wherein said body portion, distal end portion, and proximal end portion are of substantially the same radial extent prior to deployment, and wherein said proximal end portion and said distal end portion radially expand to a greater extent than said body portion radially expands upon said deployment.

18. The thin film occlusion device of claim 16, further comprising a support structure of the occlusion device for supporting at least one of said distal end portion, proximal end portion, and body portion.

19. The thin film occlusion device of claim 16, further comprising a plurality of thin film layers, each having a plurality of pores, and at least some of said pores of one of said film layers are not in full alignment with any pore of another of said film layers.

20. The thin film occlusion device of claim 16, wherein said body portion, distal end portion, and proximal end portion are comprised of a material having shape memory properties.

21. The thin film occlusion device of claim 20, wherein said material having shape memory properties is nitinol.

22. The thin film occlusion device of claim 21, wherein said nitinol is a martensite thin film.

23. The thin film occlusion device of claim 21, wherein said nitinol is an austenite thin film that transitions from martensite to austenite upon exposure to human body temperature.

* * * * *